US010165934B2

United States Patent
Igarashi et al.

(10) Patent No.: US 10,165,934 B2
(45) Date of Patent: Jan. 1, 2019

(54) ENDOSCOPE APPARATUS WITH ADDITION OF IMAGE SIGNALS

(71) Applicant: OLYMPUS CORPORATION, Tokyo (JP)

(72) Inventors: Makoto Igarashi, Hachioji (JP); Yasunori Morita, Hachioji (JP); Kazuhiro Takizawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/334,378

(22) Filed: Oct. 26, 2016

(65) Prior Publication Data

US 2017/0042413 A1 Feb. 16, 2017

Related U.S. Application Data

(63) Continuation of application No. PCT/JP2015/054211, filed on Feb. 17, 2015.

(30) Foreign Application Priority Data

Jul. 9, 2014 (JP) .................................. 2014-141656

(51) Int. Cl.
A61B 1/06 (2006.01)
A61B 1/04 (2006.01)
(Continued)

(52) U.S. Cl.
CPC .............. *A61B 1/0638* (2013.01); *A61B 1/00* (2013.01); *A61B 1/00006* (2013.01);
(Continued)

(58) Field of Classification Search
CPC . A61B 1/045; A61B 1/00006; A61B 1/00009; A61B 1/0661; G02B 23/2461; G02B 23/2484
(Continued)

(56) References Cited

U.S. PATENT DOCUMENTS 8,721,532 B2   5/2014   Takei et al.
9,326,664 B2   5/2016   Takei et al.
(Continued)

FOREIGN PATENT DOCUMENTS

CN   103491847 A   1/2014
CN   104717917 A   6/2015
(Continued)

OTHER PUBLICATIONS

International Search Report dated May 12, 2015 issued in PCT/JP2015/054211.
(Continued)

*Primary Examiner* — John P Leubecker
*Assistant Examiner* — William Chou
(74) *Attorney, Agent, or Firm* — Scully, Scott, Murphy & Presser, P.C.

(57) ABSTRACT

An endoscope apparatus has an image pickup device having a first pixel having a sensitivity in a predetermined wavelength band, and a second pixel having a sensitivity in a wavelength band including a part of the predetermined wavelength band, a light source section configured to generate a light for irradiating a subject, an intensity of which reaches a peak in the part of the predetermined wavelength band to which the second pixel has a sensitivity, and an addition section configured to generate an addition signal obtained by adding a first image pickup signal obtained by receiving a return light from the subject at a time of the subject being irradiated in the first pixel, and a second image pickup signal obtained by receiving a return light from the subject in the second pixel.

9 Claims, 11 Drawing Sheets

(51) Int. Cl.
*A61B 1/00* (2006.01)
*A61B 1/05* (2006.01)
*A61B 1/07* (2006.01)
*G02B 23/24* (2006.01)
*G02B 5/22* (2006.01)

(52) U.S. Cl.
CPC ...... *A61B 1/00009* (2013.01); *A61B 1/00045* (2013.01); *A61B 1/04* (2013.01); *A61B 1/051* (2013.01); *A61B 1/0669* (2013.01); *A61B 1/0684* (2013.01); *A61B 1/07* (2013.01); *G02B 23/2423* (2013.01); *G02B 5/22* (2013.01); *G02B 23/2461* (2013.01); *G02B 23/2484* (2013.01)

(58) Field of Classification Search
USPC ....... 600/109, 110, 160, 178, 179, 180, 181, 600/182; 348/45, 65, 69, 70
See application file for complete search history.

(56) References Cited

U.S. PATENT DOCUMENTS

| | | |
|---|---|---|
| 2003/0176768 A1 | 9/2003 | Gono et al. |
| 2006/0198551 A1 | 9/2006 | Abe et al. |
| 2009/0141125 A1* | 6/2009 | Yamazaki ............ A61B 1/0638 348/70 |
| 2013/0096376 A1 | 4/2013 | Takei et al. |
| 2015/0022647 A1* | 1/2015 | Takei ................. A61B 1/00186 348/70 |

FOREIGN PATENT DOCUMENTS

| | | |
|---|---|---|
| EP | 1302152 A1 | 4/2003 |
| EP | 1698271 A1 | 9/2006 |
| EP | 2319390 A1 | 5/2011 |
| EP | 2 896 354 A1 | 7/2015 |
| JP | 2002-095635 A | 4/2002 |
| JP | 2005-319212 A | 11/2005 |
| JP | 2006-239203 A | 9/2006 |
| JP | 2008-035470 A | 2/2008 |
| JP | 2010-193421 A | 9/2010 |
| JP | 2011-092690 A | 5/2011 |
| JP | 2012-170639 A | 9/2012 |
| WO | WO 2002/007588 A1 | 1/2002 |

OTHER PUBLICATIONS

Japanese Office Action dated Apr. 26, 2016 issued in Japanese Patent Application No. 2015-561814.
Extended Supplementary European Search Report dated Dec. 4, 2017 in European Patent Application No. 15 81 8882.1.

* cited by examiner

ENDOSCOPE APPARATUS WITH ADDITION OF IMAGE SIGNALS

CROSS REFERENCE TO RELATED APPLICATION

This application is a continuation application of PCT/JP2015/054211 filed on Feb. 17, 2015 and claims benefit of Japanese Application No. 2014-141656 filed in Japan on Jul. 9, 2014, the entire contents of which are incorporated herein by this reference.

BACKGROUND OF INVENTION

1. Field of the Invention

The present invention relates to an endoscope apparatus that generates an endoscopic image by using illuminating lights of a plurality of wavelength bands.

2. Description of the Related Art

Conventionally, in a medical field, various kinds of low-invasive examinations and surgical operations using endoscopes have been performed. A surgeon inserts an endoscope into a body cavity, observes an object an image of which is picked up by an image pickup apparatus provided at a distal end portion of an endoscope insertion portion, and can perform treatment to a lesion part by using a treatment instrument inserted through an inside of a treatment instrument channel in accordance with necessity. A surgical operation using an endoscope does not carry out a laparotomy or the like, and therefore has the merit of putting less physical burden on a patient.

Further, some of endoscope apparatuses are capable of performing not only normal observation using a white color light but also capable of performing special light observation using a special light such as an infrared light in order to observe internal blood vessels.

For example, Japanese Patent Application Laid-Open Publication No. 2011-92690 as a first conventional example, discloses R, G and B filters that partially overlap one another in FIG. 3 in the Publication, and respectively transmit lights of different wavelength bands, and details of generating a first to a third narrow band image pickup signals by sequentially turning on and causing a first to a third narrow band light sources to emit a first to a third narrow band lights. A third narrow band light N3 is a narrow band light in overlapping wavelength bands in the G and B filters.

Further, Japanese Patent Application Laid-Open Publication No. 2010-193421 as a second conventional example discloses R, G and B filters having such transmittances that include wavelength bands partially overlapping one another, and details of simultaneously emitting special lights 1, 2 and 3 respectively having different light emission wavelength bands (paragraph [0064] in the publication), and details of selectively emitting the special lights 1, 2 and 3 (paragraph [0068] in the publication).

SUMMARY OF THE INVENTION

An endoscope apparatus of one aspect of the present invention has an image pickup device having a first pixel having a sensitivity in a predetermined wavelength band, and a second pixel having a sensitivity in a wavelength band including a part of the predetermined wavelength band, a light source section configured to generate a light for irradiating a subject, an intensity of which reaches a peak in the part of the predetermined wavelength band to which the second pixel has a sensitivity, and an addition section configured to generate an addition signal obtained by adding a first image pickup signal obtained by receiving a return light from the subject at a time of the subject being irradiated in the first pixel, and a second image pickup signal obtained by receiving a return light from the subject in the second pixel.

DETAILED DESCRIPTION OF THE PREFERRED EMBODIMENT(S)

Hereinafter, an embodiment of the present invention will be described with reference to the drawings.

(First Embodiment)

Figure 1:
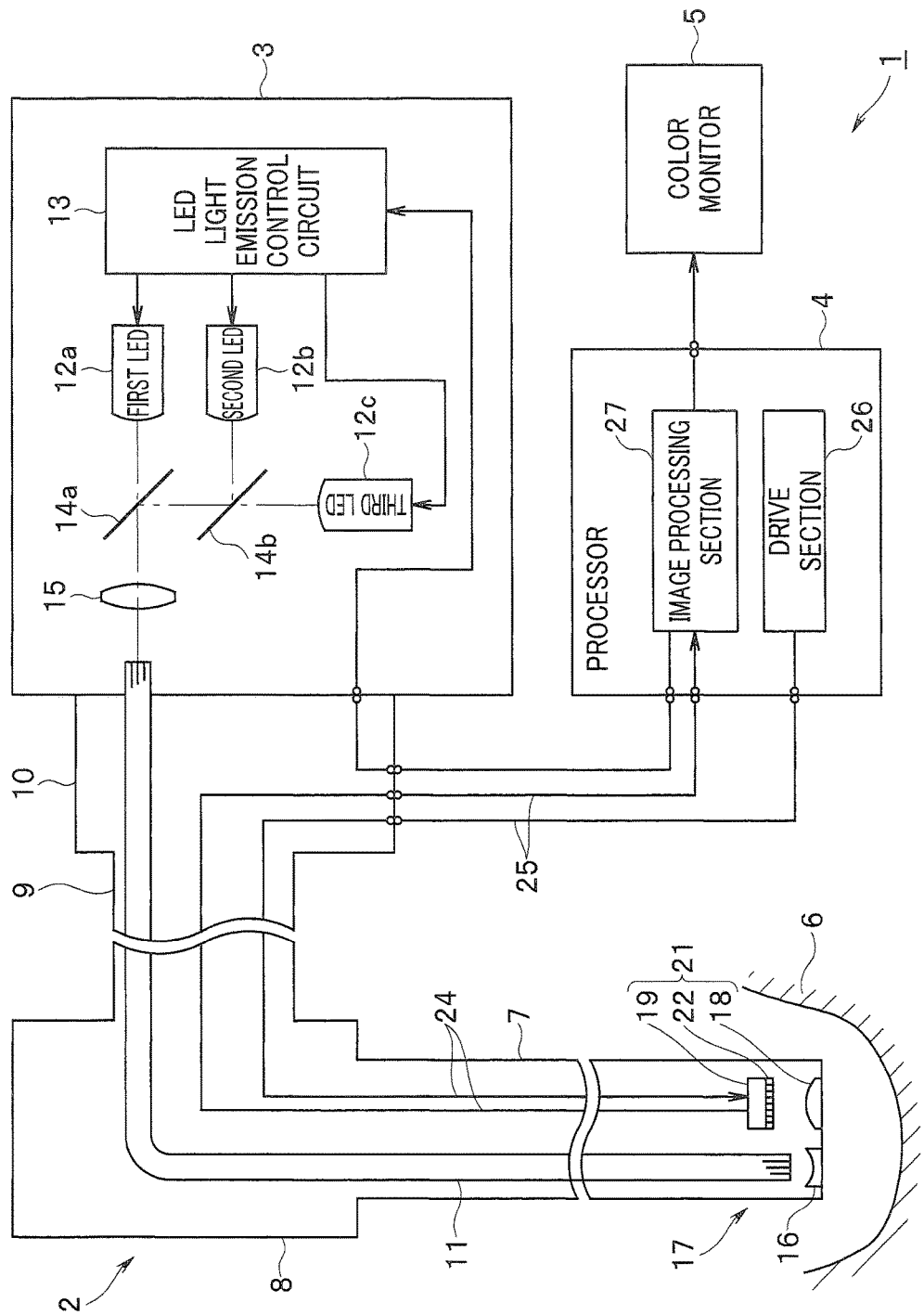
FIG. 1 is a diagram showing an entire configuration of an endoscope apparatus of a first embodiment of the present invention.

As shown in FIG. 1, an endoscope apparatus 1 of a first embodiment of the present invention has an endoscope 2 that is inserted into a body or a body cavity, a light source apparatus 3 configured to supply an illuminating light to the endoscope 2, a processor 4 configured to drive an image pickup section loaded on the endoscope 2, and to be as an image processing apparatus configured to perform image processing to an image pickup signal of an image which is picked up, and a color monitor 5 configured to form a display section (43 in FIG. 2) configured to display an image of a display image signal as an endoscopic image by receiving the display image signal generated by the processor 4.

The endoscope 2 has an elongated insertion portion 7 that is inserted into a subject 6, an operation portion 8 provided at a rear end of the insertion portion 7, and a cable 9 extended from the operation portion 8, and a connector 10 provided at an end portion of the cable 9 is detachably connected to the light source apparatus 3.

A light guide 11 that transmits an illuminating light is inserted through an inside of the endoscope 2, and a rear end (an end portion) of the light guide 11 becomes an incident end portion in the connector 10.

The light source apparatus 3 has a first light emitting diode (abbreviated as a first LED) 12a, a second LED 12b and a third LED 12c as a plurality of light sources that generate illuminating lights. Further, an LED light emission control circuit 13 that forms a light emission control circuit (a light emission control section) in the light source apparatus 3 supplies a power supply that causes the LEDs 12a, 12b and 12c to emit lights, varies currents or the like that are supplied to the LEDs 12a, 12b and 12c, and controls light emission amounts.

A light emitted by the LED 12a selectively passes through a dichroic mirror 14a, and is condensed by a condensing lens 15. Further, a light emitted by the LED 12b is selectively reflected by a dichroic mirror 14b, is selectively reflected by the dichroic mirror 14a, and is condensed by the condensing lens 15. A light emitted by the LED 12c selectively passes through the dichroic mirror 14b, is selectively reflected by the dichroic mirror 14a, and is condensed by the condensing lens 15.

The lights respectively emitted by the LEDs 12a, 12b and 12crespectively become a first illuminating light L1, a second illuminating light L2 and a third illuminating light L3, and the illuminating lights composed of the first illuminating light L1, the second illuminating light L2 and the third illuminating light L3 are condensed by the condensing lens 15 and are incident on the incident end portion of the light guide 11.

The light guide 11 transmits the illuminating lights which are incident and further emits the illuminating lights to a mucosa 6a side in the subject 6 via an illumination lens 16 from a distal end face of the light guide 11 that is disposed at a distal end portion of the insertion portion 7, and illuminates the mucosa 6a side. The LEDs 12a, 12b and 12c, the dichroic mirrors 14a and 14b, the light emission control circuit 13, the condensing lens 15, the light guide 11 and the illumination lens 16 form an illumination section 17 configured to illuminate the mucosa 6a side in the subject 6. Note that the light guide 11 and the illumination lens 16 can be also said to configure the illumination section 17.

Figure 2:
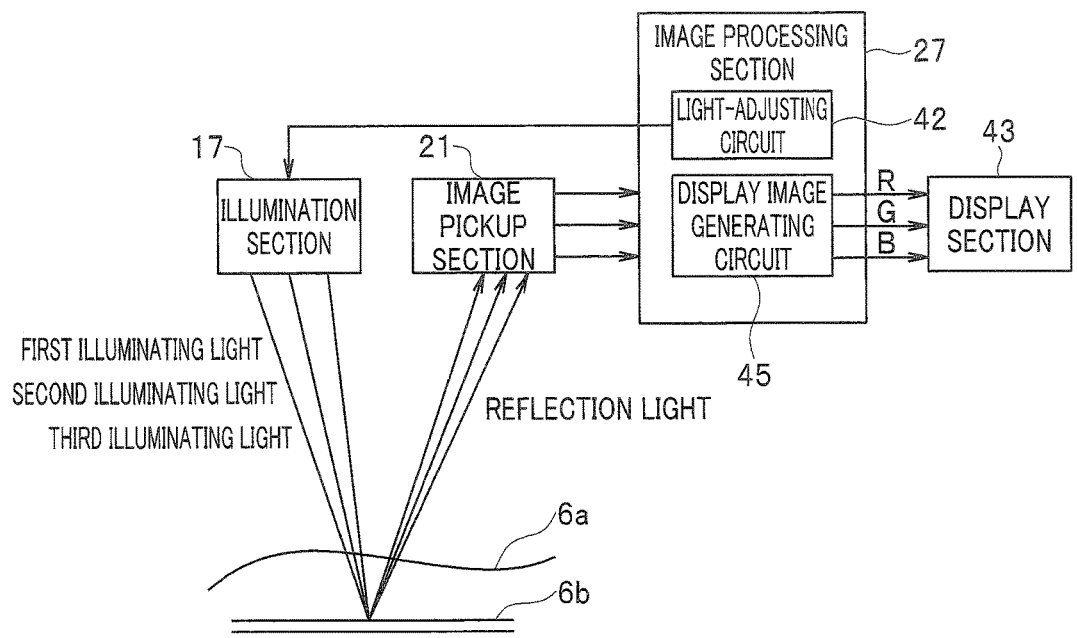
FIG. 2 is a diagram showing a functional configuration of the first embodiment.

FIG. 2 shows a state where the mucosa 6a side is illuminated by the illumination section 17. As shown in FIG. 1, at the distal end portion of the insertion portion 7, an observation window is provided adjacently to the illumination lens 16 disposed in an illuminating window, an objective lens 18 is attached to the observation window, and in an image formation position, an image pickup surface 19a (refer to FIG. 3) of an image pickup device 19 such as a charge-coupled device (abbreviated as a CCD) is disposed. The objective lens 18 and the image pickup device 19 form an image pickup section 21 configured to receive a reflection light forming a return light from the mucosa 6a side which is illuminated with the illumination section 17 and pick up an image of the mucosa 6a side.

Figure 3:
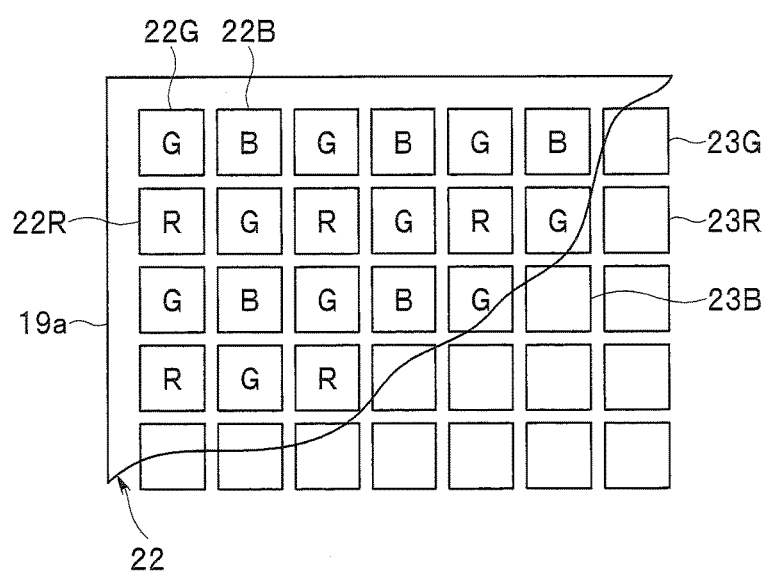
FIG. 3 is a diagram showing a pixel array including color filters of an image pickup device.

The image pickup device 19 in the present embodiment has a color filter 22 having three R, G and B filters 22R, 22G and 22B configured to separate a light forming an optical image that is formed on the image pickup surface 19a to lights of three wavelength bands. FIG. 3 shows a pixel array in the image pickup surface 19a.

As shown in FIG. 3, on the image pickup surface 19a, pixels that configure light receiving elements that perform photoelectric conversion are disposed two-dimensionally, and in front of the respective pixels, the R, G and B filters 22R, 22G and 22B configured to transmit lights of the wavelength bands of red (R), green (G) and blue (B) respectively are regularly disposed by pixel unit whereby the primary color Bayer type of color filter 22 is formed. In a case of FIG. 3, the array is such that first arrays where the G and B filters 22G and 22B are arranged in a horizontal direction, and second arrays where the R and G filters 22R and 22G are arranged in the horizontal direction are alternately repeated in a vertical direction. In the present description, respective pixels that receive lights that respectively pass through the R, G and B filters 22R, 22G and 22B are respectively described as pixels 23R, 23G and 23B as shown in FIG. 3.

In the case of FIG. 3, four pixels formed of two pixels in the vertical direction and two pixels in the horizontal direction become an array pixel of one unit that is required to form one color pixel, and in the processor 4, R, G and B signals are generated at each array pixel that is to be the unit.

Figure 4:
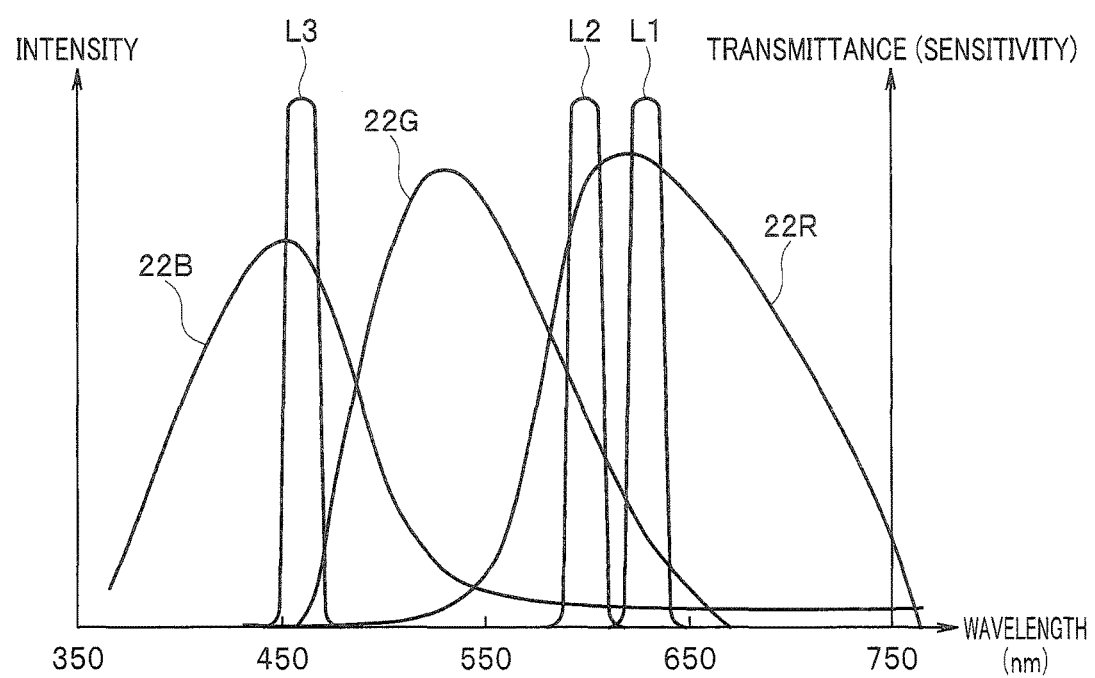
FIG. 4 is a diagram showing wavelength bands of lights generated by LEDs as light sources of a light source apparatus with characteristics of a spectral sensitivity of the image pickup device.

FIG. 4 shows transmission characteristics of the R, G and B filters 22R, 22G and 22B that configure the color filter 22 to wavelengths. Further, when the respective pixels receive lights that respectively pass through the R, G and B filters 22R, 22G and 22B, the characteristics of sensitivities to the wavelengths in the respective pixels are shown.

Further, FIG. 4 shows characteristics of intensity distributions of the first illuminating light L1 as a first light, a second illuminating light L2 as a second light and a third illuminating light L3 as a third light that are respectively generated by the above described three LEDs 12a, 12b and 12c. In the present description, the first light is used in the same meaning as the first illuminating light L1, and the same applies to the second light and the third light.

As shown in FIG. 4, the transmission characteristics of the R, G and B filters 22R, 22G and 22B to the wavelengths partially overlap one another respectively, and therefore the sensitivities of the pixels that receive the lights that respectively pass through the R, G and B filters 22R, 22G and 22B have also the characteristics partially overlapping one another.

The first illuminating light L1, the second illuminating light L2 and the third illuminating light L3 are lights in a narrow band, in which intensities reach peaks in a vicinity of 630 nm, in a vicinity of 600 nm and in a vicinity of 460 nm, respectively, and full widths at half maximum become approximately 10 to 30 nm.

Only the pixel 23B that receives the light passing through the B filter 22B substantially has a sensitivity to a reflection light from the subject 6 side by the third illuminating light L3 in which the intensity reaches the peak in the vicinity of 460 nm. In other words, the light source apparatus 3 generates the third illuminating light L3 to which (the pixels 23R and 23G forming) the first and the second pixels do not have sensitivities, besides the first and the second illuminating lights L1 and L2.

In contrast with this, both the pixel 23G that receives the light passing through the G filter 22G, and the pixel 23R that receives the light passing through the R filter 22R have sensitivities to a reflection light from the subject side by the first illuminating light L1 in which the intensity reaches the peak in the vicinity of 630 nm, and a reflection light from the subject side by the second illuminating light L2 in which the intensity reaches the peak in the vicinity of 600 nm.

For example, to the reflection light from the subject 6 side by the first illuminating light L1 which reaches the peak in 630 nm, the sensitivity of the pixel (for example, the first pixel) 23R of the R filter 22R is much larger than the sensitivity of the pixel (for example, the second pixel) 23G of the G filter 22G.

To the reflection light from the subject 6 side by the second illuminating light L2 which reaches the peak in 600 nm, the sensitivity of the pixel 23R of the R filter 22R is larger than the sensitivity of the pixel 23G of the G filter 22G, but is smaller than in a case of the first illuminating light L1.

Further, the pixel 23R of the R filter 22R picks up an image with the highest sensitivity to the reflection light from the subject 6 side by the first illuminating light L1 that reaches the peak in 630 nm, and the reflection light from the subject 6 side by the second illuminating light L2 that reaches the peak in 600 nm, but the image cannot be picked up with the respective reflection lights of 600 nm and 630 nm being separated.

Consequently, in the present embodiment, the first illuminating light L1 and the second illuminating light L2 are time-divided and illumination is performed alternately, and since only the pixel (the third pixel) 23B of the B filter 22B substantially has the sensitivity to the reflection light from the subject side by the third illuminating light L3, continuous illumination is performed concerning the third illuminating light L3. The LED light emission control circuit 13 performs control so as to cause the LED 12c to emit light all the time, and cause the LEDs 12a and 12b to emit light alternately in contrast with this (refer to FIG. 6).

Note that although in the present embodiment, the respective lights of 630 nm, 600 nm and 460 nm as the lights that reach the peaks are respectively explained as the first illuminating light L1, the second illuminating light L2 and the third illuminating light L3 in sequence from longer wavelengths, the light of 600 nm can be also defined or interpreted as the first illuminating light L1 (or the first light) and the light of 630 nm can be also defined or interpreted as the second illuminating light L2 (the second light), because the case where an image is picked up with the first illuminating light L1 and the case where an image is picked up with the second illuminating light L2 have qualitatively similar characteristics.

In the characteristic chart in FIG. 4, in the light of 630 nm, the sensitivity of the pixel 23G is much smaller as compared with the sensitivity of the pixel 23R, whereas in the light of 600 nm, the sensitivity of the pixel 23G is higher (larger) than in the former case (that is, in the case of 630 nm). Consequently, if an addition signal obtained by adding image pickup signals of the two pixels is generated when the light of 600 nm is set as the first illuminating light L1, and the light of 600 nm is used as the illuminating light, an SNR can be made sufficiently larger than in a case where an image pickup signal is generated from only one pixel.

One ends of signal lines 24 inserted through the inside of the endoscope 2 are connected to the above described image pickup device 19, and the other ends of the signal lines 24 reach contact points of the connector 10. The contact points of the connector 10 are further detachably connected to the processor 4 via signal lines 25 in the connection cable.

The processor 4 has a drive section 26 configured to generate an image pickup device drive signal that drives the image pickup device 19, and an image processing section (or an image processing circuit) 27 that performs image processing for an image pickup signal outputted from the image pickup device 19, and generates a display image signal that is color-displayed in the color monitor 5.

The image pickup device drive signal is applied to the image pickup device 19 from the drive circuit forming the drive section 26, whereby the image pickup device 19 outputs an image pickup signal that is photoelectrically converted, to the image processing section 27.

The display image signal which is generated by the image processing section 27 is outputted to the color monitor 5, and the image which is picked up by the image pickup device 19 is displayed as an endoscopic image. In the present embodiment, as described above, the mucosa 6a of the subject 6 is irradiated with the three narrow band lights in which the wavelengths where the intensities reach the peaks differ from one another, and an image is picked by the image pickup device 19 including the color filter 22.

Penetration depths in a depth direction in a vicinity of an epithelium of the mucosa 6a shown in FIG. 2 of the narrow band lights differ in accordance with wavelengths of the narrow band lights, and therefore image information in which a running state of blood vessels in the vicinity of the epithelium of the mucosa 6a is selectively extracted in accordance with the wavelengths of the narrow band lights can be acquired.

More specifically, the narrow band light of 630 nm has the largest penetration depth, and when an image is picked up under irradiation of the narrow band light, information on a running state of a large diameter blood vessel 6b at a deep part side can be acquired. Further, the light of 600 nm has a slightly shorter wavelength than 630 nm, and therefore is suitable to acquire information on a running state of a blood vessel in a region which is slightly shallower than under the light of 630 nm. In other words, when an image is picked up under the narrow band lights of the wavelengths of 630 nm and 600 nm, the information on the running state of the large diameter blood vessel 6b and the information on the running state of the blood vessel that runs in the vicinity of a depth position which is slightly shallower than the large diameter blood vessel 6b can be acquired.

Further, with the narrow band light of 460 nm, information on a running state of capillary vessels and the like that run in a position at a shallow depth in a vicinity of the epithelium of the mucosa 6acan be acquired. Subsequently, as described later, the image pickup signals of images picked up by the image pickup device 19 under irradiation of the three narrow band lights are respectively assigned to different colors and are displayed as a color endoscopic image, whereby a surgeon can visibly recognize the running state of the blood vessels in the vicinity of the epithelium of the mucosa 6a.

Accordingly, when a surgical operation is performed with use of an electric knife or the like under observation by the endoscope apparatus 1 of the present embodiment, a state of a change by excision or the like can be visually recognized with the running state of the large diameter blood vessel 6b especially at the deep portion side, and therefore the surgical operation can be easily performed smoothly.

Figure 5:
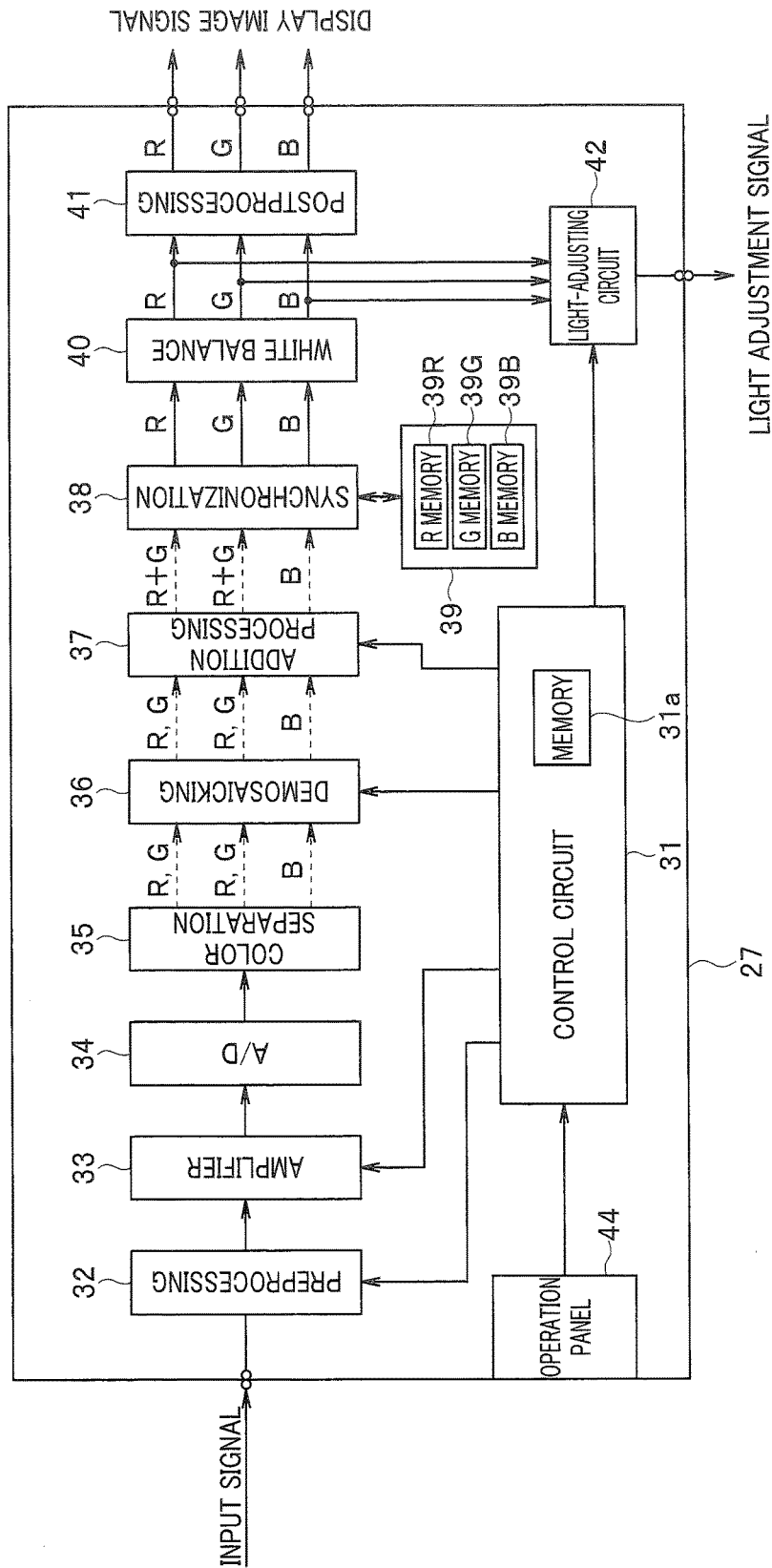
FIG. 5 is a block diagram showing a configuration of an image processing section.

FIG. 5 shows a configuration of the image processing section 27. The image processing section 27 has a control circuit 31 configured to perform control of a plurality of circuits in the image processing section 27, an image pickup signal as an input signal that is inputted to the image processing section 27 is inputted to a preprocessing circuit 32, and the preprocessing circuit 32 performs processing of determining a black level by clamping OB (optical black) in the image pickup signal, correction processing to a defective pixel of the image pickup device 19, noise reduction processing and the like by using parameter values that are stored in advance in a memory 31a in the control circuit 31.

An output signal of the preprocessing circuit 32 is inputted to an amplifier 33 for gain adjustment, and gain of the amplifier 33 is adjusted based on a wave detection value obtained by being subjected to light adjustment and wave detection which will be described later, whereby brightness of the endoscopic image that is displayed on the color monitor 5 is adjusted based on an image pickup signal. The output signal from the amplifier 33 is inputted to an A/D conversion circuit 34, and the analog image pickup signal is converted into a digital image pickup signal.

The output signal of the A/D conversion circuit 34 is inputted to a color separation circuit 35, and the color separation circuit 35 separates the inputted image pickup signal into color components in accordance with the array of the R, G and B filters 22R, 22G and 22B of the image pickup device 19 to output signals.

As described above, the third illuminating light L3 is the illuminating light that performs continuous illumination, whereas the first illuminating light L1 and the second illuminating light L2 are frame-sequential illuminating lights that perform illumination alternately (time-division). The color separation circuit 35 continuously outputs a signal (abbreviated as B in FIG. 5) of an image picked up by the pixel 23B of the B filter 22B under the third illuminating light L3 (shown by a solid line in FIG. 5), whereas the color separation circuit 35 alternately outputs signals (abbreviated as R and G in FIG. 5) of an image picked up by the pixels 23R and 23G of the R and G filters 22R and 22G under the first illuminating light L1 and the second illuminating light L2 (shown by dotted lines in FIG. 5).

The output signals of the color separation circuit 35 are inputted to a demosaicking circuit 36 as an interpolation processing circuit, and interpolation processing is performed. The interpolation processing is disclosed, for example, in Japanese Patent Application Laid-Open Publication No. 2008-35470. Interpolation processing is not limited to the interpolation processing like this, and interpolation processing such as bicubic that is known to the public may be performed.

The output signal of the demosaicking circuit 36 is inputted to the addition processing circuit 37 that forms an addition section, and the addition processing circuit 37 adds a signal of an image that is picked up in a frame-sequential manner, and outputs the signal to a synchronization circuit 38. The synchronization circuit 38 has a memory section 39 including three memories 39R, 39G and 39B, for example, to perform synchronization.

As described later, a first addition signal that is obtained by picking up an image under the first illuminating light L1, and is added is outputted to (the memory 39R of) the synchronization circuit 38 so that the synchronization circuit 38 outputs the first addition signal as an R signal of an R channel, and a second addition signal that is obtained by picking up an image under the second illuminating light, and is added is outputted to (the memory 39G of) the synchronization circuit 38 so that the synchronization circuit 38 outputs the addition signal as a G signal of a G channel. Note that in FIG. 5, a configuration in which the memory section 39 is disposed outside the synchronization circuit 38 is shown, but a configuration in which the memory section 39 is provided inside the synchronization circuit 38 may be adopted.

Note that the added R+G and R+G signals shown by dotted lines from the addition processing circuit 37 in FIG. 5 simply show the first addition signal obtained by adding the signals of an image picked up under the first illuminating light, and the second addition signal obtained by adding the signals of an image picked up under the second illuminating light. Further, the R+G and R+G signals are respectively stored in the different memories 39R and 39G in the synchronization circuit 38, and the synchronization circuit 38 outputs the R+G and R+G signals as the R and G signals of the R and G channels to be different colors from each other.

Further, the addition processing circuit 37 outputs a B signal of the image picked up by the pixel 23B of the B filter 22B to the synchronization circuit 38 directly (without being added), and the B signal is stored in the memory 39B. The synchronization circuit 38 outputs the B signal stored in the memory 39B as the B signal of a B channel simultaneously with the R and G signals of the R and G channels.

In this way, the synchronization circuit 38 forms a color assigning section (a color assigning circuit) or an image generation section that generates an image in which the first addition signal, the second addition signal and the B signal by the pixel 23B forming the third pixel are respectively assigned to different colors.

The synchronization circuit 38 outputs signals (R, G and B shown by solid lines in FIG. 5) that are synchronized by synchronously reading the three image pickup signals that are obtained by picking up an image under illumination of the time-division illuminating lights L1 and L2 and the continuous illuminating light L3, and are stored in the three memories 39R, 39G and 39B to a white balance circuit 40.

The white balance circuit 40 is configured by three variable gain amplifiers, for example, and performs adjustment so that signal levels of the two signals R and B are equal to a signal level of the G signal, for example, in three of the R, G and B signals that are outputted from the white balance circuit 40 in a case where an image of a subject of a white color to be a reference is picked up. More specifically, variable adjustment of gains of the three variable gain amplifiers is performed so that signal levels of the first addition signal, the second addition signal and the B signal are equal to one another.

The white balance circuit 40 outputs output signals to a postprocessing circuit 41 and a light-adjusting circuit 42. The postprocessing circuit 41 performs gradation conversion processing, color enhancement processing, and contour enhancement processing by using a gradation conversion coefficient, a color conversion coefficient and a contour enhancement coefficient that are stored in the memory 31a of the control circuit 31 in advance, for example, and outputs the R, G and B signals after the processing to the color monitor 5 that configures the display section (or a display apparatus) 43 as display image signals. The color monitor 5 displays an image of the subject 6 which is picked up by the image pickup section 21.

The light-adjusting circuit 42 generates a luminance signal Y from the signal inputted from the white balance circuit 40, generates a signal of an average value of one frame to several frame periods of the luminance signal Y as a brightness signal, and outputs a signal which is a difference value from brightness targeted to the LED light emission control circuit 13 as a light adjustment signal.

In a case of the light adjustment signal for the brightness signal which is smaller than the brightness of the light adjustment target, the light adjustment signal is a light adjustment signal that causes the LED light emission control circuit 13 to increase light emission amounts of the LEDs 12a, 12b and 12c, and in a case of the light adjustment signal for the brightness signal that is larger than the brightness of the light adjustment target, the light adjustment signal is a light adjustment signal that causes the LED light emission control circuit 13 to decrease the light emission amounts of the LEDs 12a, 12b and 12c.

Further, the image processing section 27 or the processor 4 has an operation panel 44, and a user performs operations and inputs of setting parameters, setting target brightness and the like in the case of the image processing section 27 performing image processing from the operation panel 44, whereby the control circuit 31 performs corresponding control operations. Note that a display image generating circuit 45 that is shown in FIG. 2 is configured by the preprocessing circuit 32, the amplifier 33, . . . , and the postprocessing circuit 41 in FIG. 5, but may be defined as configured by the postprocessing circuit 41.

The endoscope apparatus 1 of the configuration as above has the image pickup device 19 having the pixel 23R which forms the first pixel having a sensitivity in the first wavelength band, and the pixel 23G which forms the second pixel having a sensitivity in the second wavelength band including a part of the aforementioned first wavelength band, the light source apparatus 3 which forms the light source section which generates the first light for irradiating the subject 6 and has the intensity reaching the peak in a part of the aforementioned first wavelength band included in the second wavelength band, and the addition processing circuit 37 which forms the addition section that generates the first addition signal obtained by adding the image pickup signal obtained by receiving the return light of the subject 6 at the time of the first light being irradiated in the first pixel, and the image pickup signal obtained by receiving the return light of the subject 6 at the time of the first light being irradiated in the second pixel.

Figure 6:
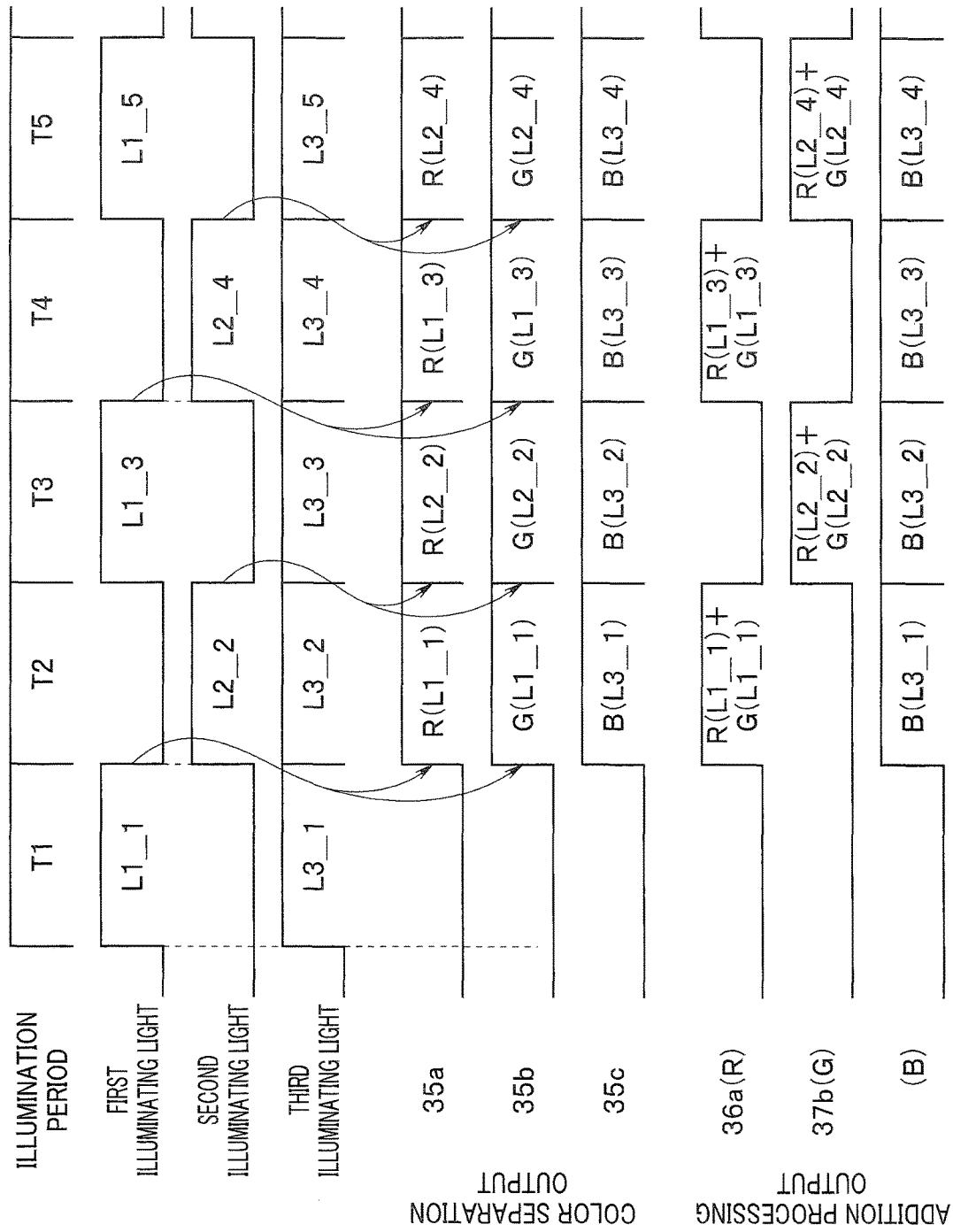
FIG. 6 is an operation explanatory view of the first embodiment.

Next, an operation of the present embodiment will be described. As described above, the surgeon inserts the endoscope 2 into the subject 6, irradiates the mucosa 6a with the illuminating light which is a narrow band light, observes a color endoscopic image displayed on the color monitor 5, and performs a surgical operation of excising a lesion part or the like by using an electric knife or the like. FIG. 6 shows a timing chart for explaining an operation in a case where a color endoscopic image is displayed on the color monitor 5 by the endoscope apparatus 1 of the present embodiment.

The light source apparatus 3 alternately generates the first illuminating light L1 and the second illuminating light L2 at each of one-frame illumination periods T1, T2, T3, . . . Ti . . . , and the alternate illuminating lights L1 and L2 are irradiated to the subject 6 side. In FIG. 6, when i of the illumination period Ti is an odd number, first illuminating lights L1_1, L1_3, L1_5, . . . are sequentially irradiated to the subject 6, and when i of the illumination period Ti is an even number, second illuminating lights L2_2, L2_4, L2_6, . . . are sequentially irradiated to the subject 6. Further, the third illuminating light L3 is continuously irradiated to the subject 6 as shown by L31, L3_2, L3_3, . . . .

At the time of irradiation of the illuminating lights as above, the image pickup device 19 receives the reflection light which is the return light from the subject 6, and outputs an image pickup signal which is subjected to photoelectric conversion to the image processing section 27. The image processing section 27 inputs the image pickup signals which go through the preprocessing circuit 32, the amplifier 33 and the A/D conversion circuit 34 to the color separation circuit 35.

The color separation circuit 35 outputs image pickup signals which are subjected to color separation from three output terminals 35a, 35b and 35c shown in FIG. 6. For example, when an image is picked up by the image pickup device 19 under the first illuminating light L1 and the third illuminating light L3 in the illumination period T1, the output terminal 35a outputs an image pickup signal R (L1_1) of an image picked up in the pixel 23R of the R filter, the output terminal 35b outputs an image pickup signal G (L1_1) of an image picked up in the pixel 23G of the G filter, and the output terminal 35c outputs an image pickup signal B (L3_1) of an image picked up in the pixel 23B of the B filter, in a period in which the illumination period T1 ends (the illumination period T2 starts).

Further, in a period in which the illumination period T2 ends (the illumination period T3 starts), the output terminal 35a outputs an image pickup signal R (L2_2) of an image picked up in the pixel 23R of the R filter, the output terminal 35b outputs an image pickup signal G (L2_2) of an image picked up in the pixel 23G of the G filter, and the output terminal 35c outputs an image pickup signal B (L3_2) of an image picked in the pixel 23B of the B filter.

Similar processing is performed in the illumination periods T3, T4, . . . etc. The output signal of the color separation circuit 35 is subjected to interpolation processing in the demosaicking circuit 36, and thereafter is inputted to the addition processing circuit 37.

As shown in FIG. 6, the addition processing circuit 37 (a first addition processing circuit 37a (R)) generates a first addition signal obtained by adding the image pickup signals R(L1_1) and G(L1_1) of an image that are respectively picked up in the pixel 23R and the pixel 23G under the first illuminating light L1.

Further, (a second addition processing circuit 37b in) the addition processing circuit 37 generates a second addition signal obtained by adding the image pickup signals R (L2_2) and G (L2_2) of an image that are respectively picked up in the pixel 23R and the pixel 23G under the second illuminating light L2. As shown in FIG. 6, addition processing in the illumination period T4, . . . etc. is similar processing. Note that the first addition processing circuit 37a (R) expresses that the generated first addition signal is stored in the R memory 39R which is assigned to the color of R in the synchronization circuit 38.

As above, in the present embodiment, in the case where the first illuminating light L1 or the second illuminating light L2 as the light the intensity of which reaches the peak in a partial wavelength region where the sensitivities in the two pixels 23R and 23G overlap each other is irradiated, the addition processing circuit 37 which forms the addition section generates the first addition signal or the second addition signal that is obtained by adding the two image pickup signals of an image respectively picked up in the two pixels 23R and 23G, whereby the addition processing circuit 37 generates an image pickup signal (an image signal) with a high SNR, and enables an endoscopic image with high image quality to be displayed.

In other words, when the subject 6 is irradiated with the light in the wavelength band to which the two pixels respectively have sensitivities (the first illuminating light L1 or the second illuminating light L2 in the present embodiment), and the return light of the light is received (or an image of the return light is picked up), the addition signal obtained by adding the image pickup signals of the two pixels is generated, whereby an image pickup signal with a higher SNR than the image pickup signal in the case where no addition is performed is generated. Note that it can be said that by performing addition, image pickup information of the two pixels is used more effectively (than in the case where addition is not performed).

The addition processing circuit 37 holds the first addition signal and the second addition signal for the two illumination periods 2T. Note that the two illumination periods 2T (T=Ti, i=1, 2, . . . ) is a generation period for the color image corresponding to one frame.

The addition processing circuit 37 allows the image pickup signal of the pixel 23B to pass through the addition processing circuit 37 without performing addition and directly outputs the image pickup signal. In FIG. 6, (B) in the addition processing output shows that the B signal outputted from the output terminal 35c of the color separation circuit 35 is directly outputted.

The first addition signal outputted from the addition processing circuit 37 is stored in the R memory 39R of the synchronization circuit 38, the second addition signal is stored in the G memory 39G, and the image pickup signal of the pixel 23B is stored in the B memory 39B respectively.

The R signal which is synchronized by the synchronization circuit 38 and is outputted from the R memory 39R, the G signal which is outputted from the G memory 39G, and the B signal which is outputted from the B memory 39B are subjected to adjustment of white balance in the white balance circuit 40.

An output signal of the white balance circuit 40 passes through the postprocessing circuit 41 to be a display image signal, and an endoscopic image is displayed in the color monitor 5. Further, the output signal of the white balance circuit 40 is inputted to the light-adjusting circuit 42, and the light emission amount of the illuminating light or the like is adjusted so that brightness of the endoscopic image displayed in the color monitor 5 becomes the brightness of the light adjustment target.

According to the present embodiment which operates as above, even when an image of the return light of the light which is emitted in the wavelength band to which the first pixel and the second pixel in the image pickup device 19 have sensitivities is picked up, a signal with a high SNR can be generated, since the addition signal is generated.

Further, since the image pickup signal or the image signal in which the first addition signal and the second addition signal are respectively assigned to different colors is generated, an endoscopic image suitable for a surgical operation and an endoscopic examination can be generated. In particular, the large diameter blood vessel 6b in the vicinity of the epithelium of the mucosa 6a is displayed in color to be easily recognized visually with use of the narrow band light in the vicinity of the wavelength especially in the border of the red and the green as the illuminating light, so that when the large diameter blood vessel 6b is cut at the time of a surgical operation, treatment of coagulation or the like can be performed in a state where a situation of a running state of the blood vessel under the treatment of coagulation or the like is easily recognized visually.

Figure 7:
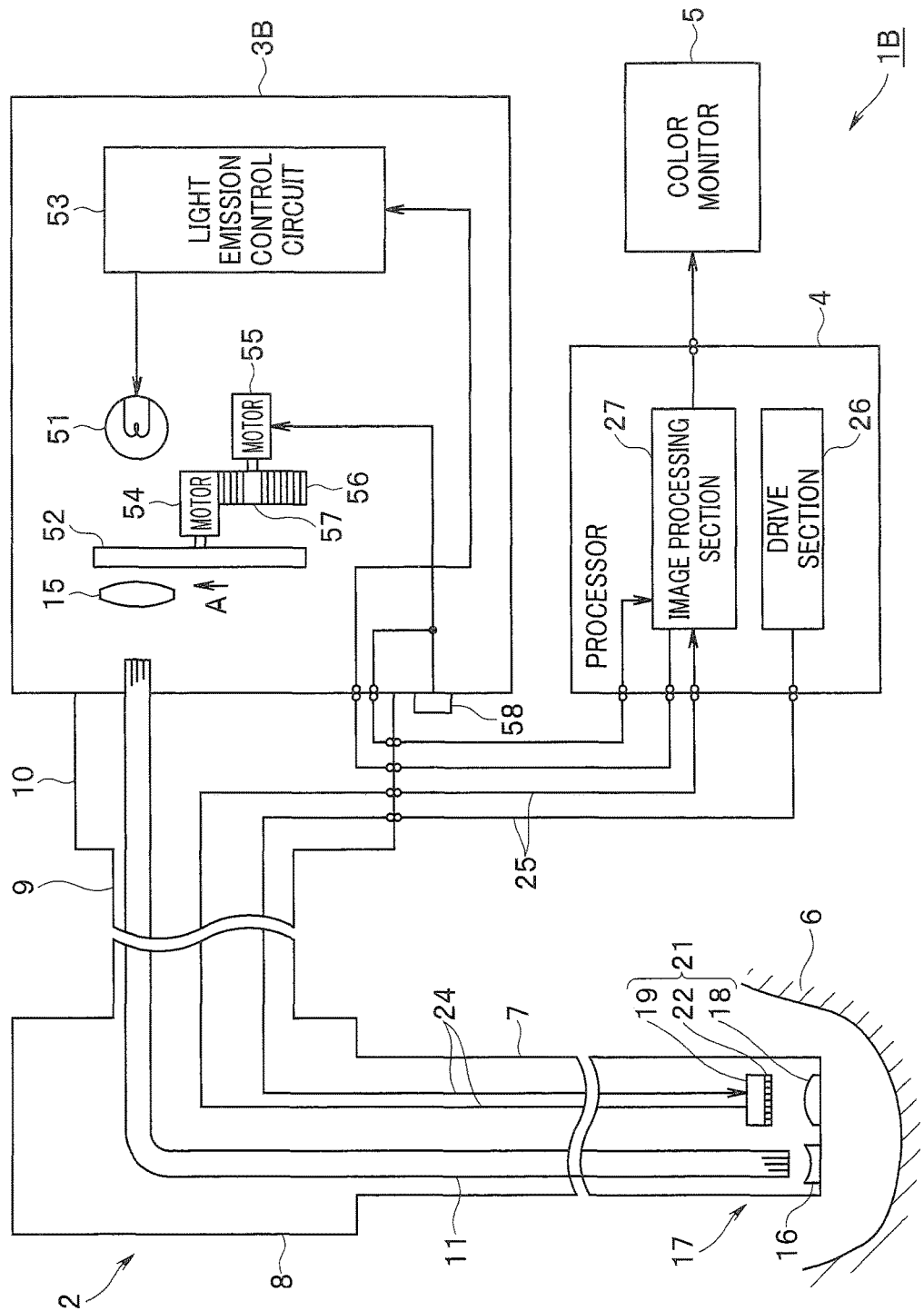
FIG. 7 is a diagram showing an entire configuration of an endoscope apparatus of a first modification of the first embodiment of the present invention.

In the aforementioned first embodiment, the configuration in the case where the light source apparatus 3 uses the LEDs 12a, 12b and 12c is shown, but the light source apparatus 3 may be configured by using a xenon lamp 51 as in an endoscope apparatus 1B of a first modification shown in FIG. 7.

The endoscope apparatus 1B of the first modification shown in FIG. 7 adopts a light source apparatus 3B having the xenon lamp 51 as a light source generating a light that covers a visible wavelength band, a rotary filter 52, a light emission control circuit 53, a motor 54 that rotates the rotary filter 52, a motor 55 that moves the rotary filter 52 and the like, instead of the LEDs 12a, 12b and 12c, the LED light emission control circuit 13, and the dichroic mirrors 14a and 14b in the light source apparatus 3 in the endoscope apparatus 1 shown in FIG. 1.

Figure 8:
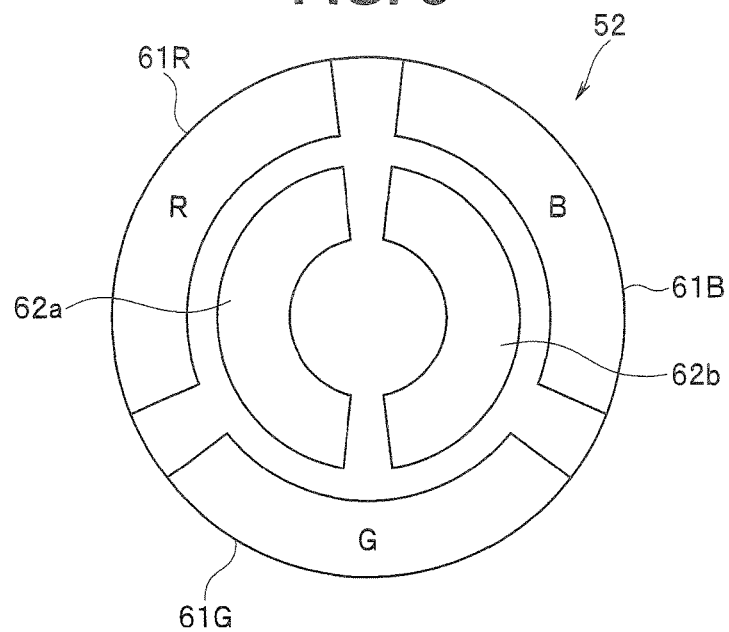
FIG. 8 is a view showing a rotary filter that is used in the endoscope apparatus in FIG. 7.

In the present modification, the rotary filter 52 includes R, G and B filters 61R, 61G and 61B, and a first filter 62a and a second filter 62b at an outer circumferential side and at an inner circumferential side as shown in FIG. 8.

The motor 54 which has a rotating shaft connected to a center of the rotary filter 52 to rotate the rotary filter 52 is attached to a rack 56, and the motor 55 includes a gear 57 that is meshed with recesses and protrusions of the rack 56. By rotation of the motor 55, the rotary filter 52, the motor 54 and the rack 56 are caused to ascend and descend so that a position of the rotary filter 52 that faces on an optical path can be switched.

Further, the light source apparatus 3B is provided with a mode change-over switch 58 that switches a normal light observation mode (a WBI mode) of emitting an illuminating light for normal light observation and a narrow band light observation mode (an NBI mode) of emitting the aforementioned narrow band light. The user can apply a mode change-over signal to the motor 55 of the light source apparatus 3B by operating the mode change-over switch 58, rotate the motor 55 and move the rotary filter 52.

By movement of the rotary filter 52, the position of the rotary filter 52 facing on the optical path is changed, and an illuminating light passing through the rotary filter 52 is switched. Note that the state shown in FIG. 7 is a state of the WBI mode in which the filter at the outer circumferential side faces on the optical path.

When the mode change-over switch 58 is operated in this state, the motor 55 to which the mode change-over signal is applied moves the rotary filter 52 in an upper direction as shown by an arrow A, and switches the state to a state of the NBI mode in which the filter at the inner circumferential side faces on the optical path.

Further, the mode change-over signal is outputted to (the image processing section 27 of) the processor 4 from the light source apparatus 3B, and the image processing section 27 performs image processing corresponding to the mode-changeover signal.

FIG. 8 shows the rotary filter 52. For example, at the outer circumferential side in the rotary filter 52, the R, G and B filters 61R, 61G and 61B that allows wavelength bands of the R, G and B of a wide band to pass through are disposed, and at the inner circumferential side, the first filter 62a and the second filter 62b of a narrow band are disposed.

Figure 9:
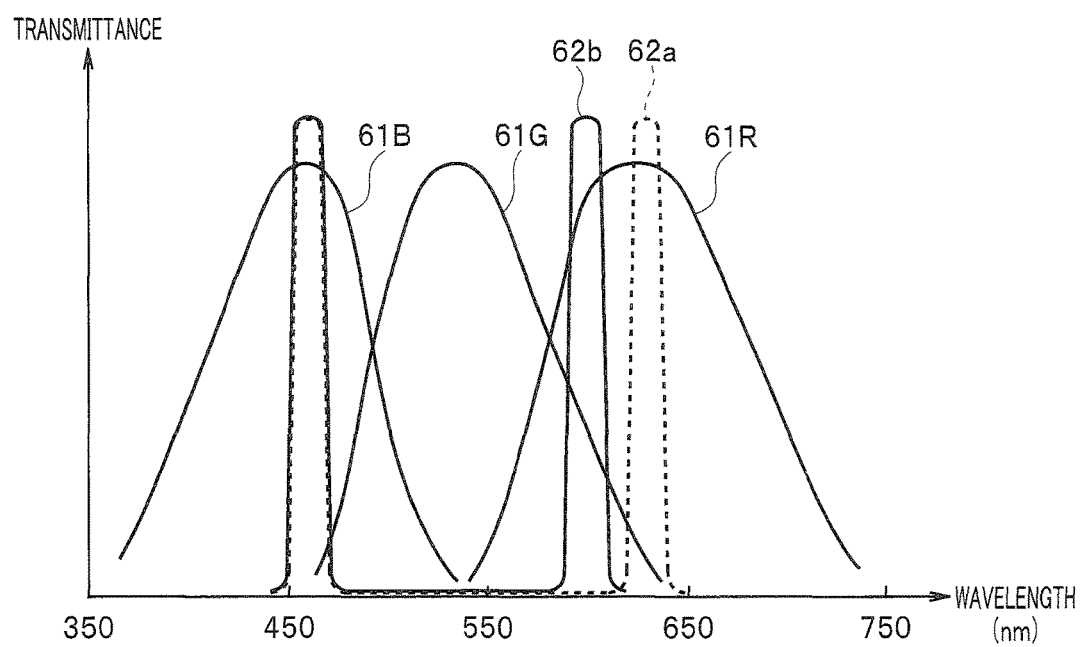
FIG. 9 is a diagram showing spectral characteristics of filters that are provided at an outer circumferential side and an inner circumferential side of the rotary filter in FIG. 8.

FIG. 9 shows spectral characteristics of the R, G and B filters 61R, 61G and 61B of a wide band, and spectral characteristics of the first filter 62a and the second filter 62b of a narrow band. The R, G and B filters 61R, 61G and 61B are set to allow the wavelength bands of R, G and B of the wide band to pass through. Note that as the R, G and B filters 61R, 61G and 61B, filters having the same characteristics as the R, G and B filters 22R, 22G and 22B in FIG. 4 may be adopted.

In contrast with the above, the first filter 62a of a narrow band (shown by a dotted line) is set to transmit narrow band lights in a vicinity of 630 nm and in a vicinity of 460 nm, and the second filter 62b of a narrow band (shown by a solid line) is set to transmit narrow band lights in a vicinity of 600 nm and in a vicinity of 460 nm.

In other words, the light source apparatus 3B in the first modification includes a first light source that simultaneously generates the first illuminating light L1 in the vicinity of 630 nm and a third illuminating light L3 in the vicinity of 460 nm, and a second light source that simultaneously generates the second illuminating light L2 in the vicinity of 600 nm and the third illuminating light L3 in the vicinity of 460 nm, and the light emission control circuit 53 controls the first light source and the second light source so that the first light source and the second light source are caused to alternately emit light and stop emitting light.

Note that in the light source apparatus 3 of the first embodiment, a similar function can be realized by a configuration as follows being adopted. In FIG. 1, the LED 12a and the LED 12c are set as the first light source, the LED 12b and the LED 12c are set as the second light source, and control is performed so that the LED light emission control circuit 13 causes the first light source and the second light source to alternately emit light and stop emitting light.

When the rotary filter 52 makes one rotation in the state of the WBI mode shown in FIG. 7, the R, G and B filters 61R, 61G and 61B are sequentially disposed on the optical path, and the light source apparatus 3B emits illuminating lights of R, G and B of a wide band to the light guide 11.

In contrast with the above, when the rotary filter 52 makes one rotation in the state of the NBI mode in which the filters at the inner circumferential side of the rotary filter 52 face on the optical path, the first filter 62a and the second filter 62b are sequentially disposed on the optical path, and the light source apparatus 3B sequentially emits the first illuminating light L1 and the third illuminating light L3 of a narrow band, and the second illuminating light L2 and the third illuminating light L3 of a narrow band to the light guide 11.

Accordingly, in the state of the NBI mode, the light source apparatus 3B continuously emits the third illuminating light L3, and alternately emits the first illuminating light L1 and the second illuminating light L2, and therefore, emits substantially the same illuminating lights as the light source apparatus 3 of the first embodiment.

Further, in the state of the NBI mode, the image processing section 27 performs substantially the same image processing as in the first embodiment.

In the state of the WBI mode, the image processing section 27 performs image processing corresponding to a frame-sequential illuminating light. More specifically, a signal of an image picked up with the light of R of a wide band which is a transmission light of the R filter 61R is stored in the R memory 39R of the synchronization circuit 38, a signal of an image picked up with the light of G of a wide band which is a transmission light of the G filter 61G is stored in the G memory 39G of the synchronization circuit 38, and a signal of an image picked up with a light of B of a wide band which is a transmission light of the B filter 61B is stored in the B memory 39B of the synchronization circuit 38.

After the signals are stored in the R, G and B memories 39R, 39G and 39B of the synchronization circuit 38, the synchronization circuit 38 simultaneously reads the signals and outputs the synchronized R, G and B signals. Subsequently, a normal light image of the WBI mode is displayed on the color monitor 5.

The present modification has substantially the same effect as the first embodiment in the state of the NBI mode. Further, the present modification also can display an image of the WBI mode.

Note that in the present modification, a visible light transmission filter that transmits a visible wavelength band may be adopted instead of the R, G and B filters 61R, 61G and 61B shown in FIG. 8. That is, as the filter at the outer circumferential side, a filter that always transmits a visible wavelength band may be adopted.

When the filter is adopted, the color separation circuit 35 in the WBI mode generates the R, G and B signals by performing separation to each of the pixels 23R, 23G and 23B respectively including the R, G and B filters 22R, 22G and 22B.

Figure 10:
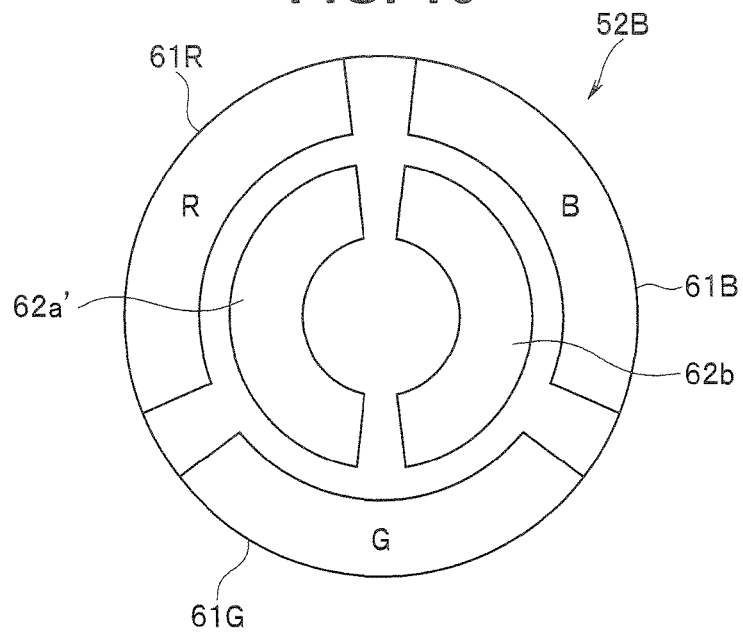
FIG. 10 is a diagram showing a rotary filter in a second modification of the first embodiment of the present invention.

An endoscope apparatus of a second modification that adopts a rotary filter 52B shown in FIG. 10 instead of the rotary filter 52 in FIG. 8 may be adopted. In the first modification, the configuration is made similar to the case where the third illuminating light L3 is irradiated substantially continuously, but in the second modification, a configuration in which the third illuminating light L3 and a fourth illuminating light L4 are illuminated alternately or in a time division manner is adopted.

The rotary filter 52B in the present modification has a configuration in which the first filter 62a, for example, in the filter at the inner circumferential side in the rotary filter 52 in FIG. 8 is changed to a first filter 62a'.

Figure 11:
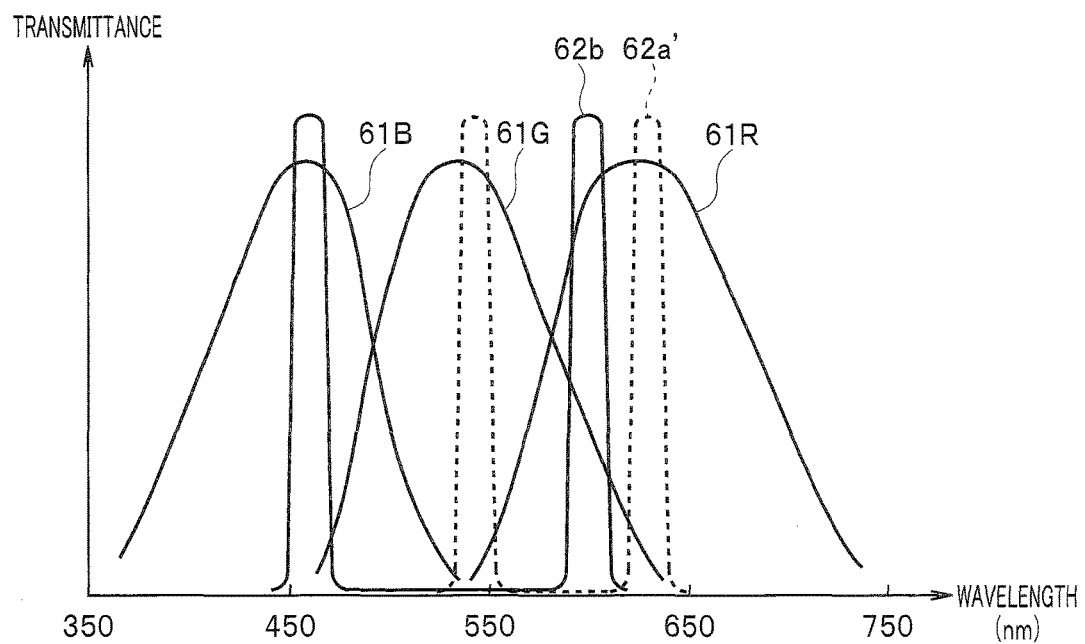
FIG. 11 is a diagram showing spectral characteristics of filters that are provided at an outer circumferential side and an inner circumferential side of the rotary filter in FIG. 10.

FIG. 11 shows spectral characteristics of filters configuring the rotary filter 52B in a case of the present modification. In FIG. 11, spectral characteristics of the filters other than the first filter 62a' are similar to the characteristics shown in FIG. 9, and the first filter 62a' shown by dotted lines have characteristics that have a peak transmittance in a vicinity of 630 nm and in a vicinity of 540 nm.

Note that the R, G and B filters 61R, 61G and 61B as the filters at the outer circumferential side are the same as in FIG. 8 in the first modification, and accordingly an operation in the WBI mode is the same as in the first modification, so that explanation of the operation will be omitted.

Figure 12:
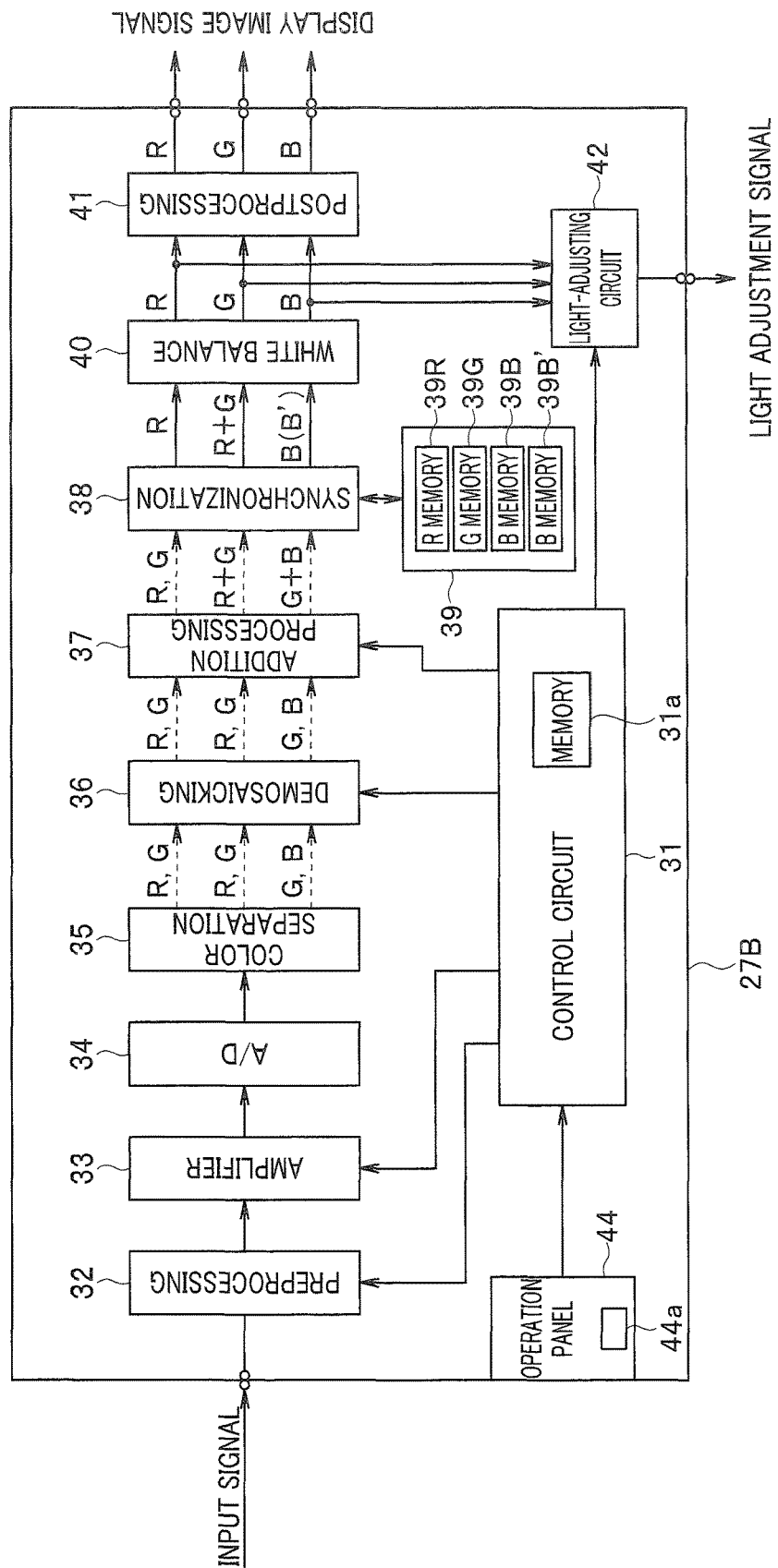
FIG. 12 is a block diagram showing a configuration of an image processing unit in the second modification.

In the present modification, in order to use the first illuminating light L1 (630 nm) in which the peak is at 630 nm, the second illuminating light L2 (600 nm) in which the peak is at 600 nm, the third illuminating light L3 (460 nm) in which the peak is at 460 nm, and the fourth illuminating light L4 (540 nm) in which the peak is at 540 nm, an image processing section 27B shown in FIG. 12 is adopted instead of the image processing section 27 shown in FIG. 5. The image processing section 27B shown in FIG. 12 further has a (second) B memory 39B' besides the three memories, as the memory section 39 in FIG. 5.

Further, in the addition processing circuit 37 in the first modification, the first addition processing circuit and the second addition processing circuit are 37a and 37b, but in the addition processing circuit 37 in the present modification, the first addition processing circuit and the second addition processing circuit are 37c and 37b (or 37b and 37c which are switched) as will be described as follows.

Further, the operation panel 44 is provided with an image selection button 44a for selecting one image in the two images when the image is displayed in the color monitor 5.

In the present modification, the R and G images in the two images are common as will be described as follows, but as the B image, an image pickup signal of an image picked up under the third illuminating light L3, and an image pickup signal of an image picked up under the fourth illuminating light L4 are made selectable. As explained in FIG. 13, the image pickup signal of an image picked up under the third illuminating light L3 is stored in the B memory 39B, for example, and the image pickup signal of an image picked up under the fourth illuminating light L4 is stored in the B memory 39B.

Subsequently, the user can select the first image and the second image by the image selection button 44a, and when the first image is selected, the control circuit 31 performs control so that the B image in the B memory 39B' corresponding to selection is outputted from the synchronization circuit 38 with the R and G images which are common, whereas when the second image is selected, the control circuit 31 performs control so that the B image in the B memory 39B which corresponds to selection is outputted from the synchronization circuit 38 with the R and G images which are common.

Next, an operation of the present modification will be described.

Figure 13:
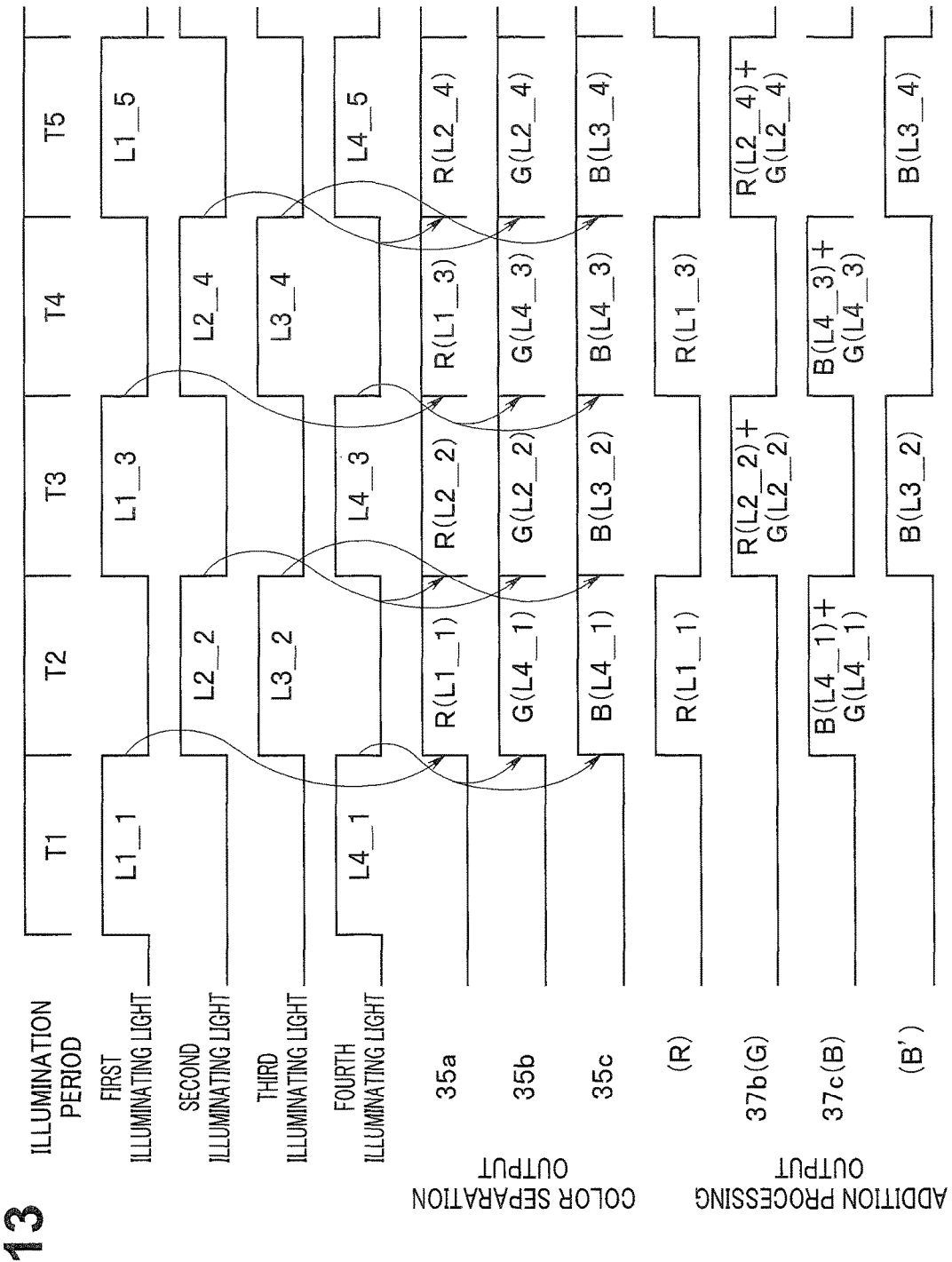
FIG. 13 is an operation explanatory view of the second modification.

FIG. 13 shows an operation explanatory diagram of the present modification. The operation explanatory diagram in FIG. 13 adopts the same description method as the operation explanatory diagram in FIG. 6, and the third illuminating light is continuous illumination in FIG. 6, whereas in the present modification, the third illuminating light L3 (460 nm) performs illumination at the same timing (even number illumination periods that are the illumination periods T2, T4, ... in FIG. 13) as the second illuminating light L2 (600 nm), and the first illuminating light L1 (630 nm) performs illumination at the same timing (odd number illumination periods that are the illumination periods T1, T3, ... in FIG. 13) as the fourth illuminating light L4 (540 nm). Note that as also mentioned in the first embodiment, the light of 600 nm may be interpreted (defined) as the first (illuminating) light, and the light of 630 nm may be interpreted (defined) as the second (illuminating) light.

When illumination is performed with the first illuminating light L1 (630 nm) and the fourth illuminating light L4 (540 nm), the pixel 23R in the image pickup device 19 has a sensitivity to a reflection light of the first illuminating light L1 (630 nm), and mainly outputs an R signal by color separation, whereas the pixel 23G has a sensitivity to a reflection light of the fourth illuminating light L4 (540 nm), and mainly outputs the G signal by color separation.

More specifically, when an image is picked up by the image pickup device 19 including the color filter 22 with the characteristics shown in FIG. 4 in the case where illumination is performed by using the first filter 62a' having (the transmittance of) the peak at 630 nm and 540 nm shown in FIG. 11, an image of the reflection light of the first illuminating light L1 that reaches the peak intensity at 630 nm, and an image of the reflection light of the fourth illuminating light L4 that reaches the peak intensity at 540 nm can be respectively picked up by being separated without color mixture by the pixel 23R of the R filter 22R and the pixel 23G of the G filter 22G.

Note that the pixel 23B receives a light with a sensitivity much lower than the pixel 23G having a high sensitivity to the reflection light of the fourth illuminating light L4 (540 nm), and outputs a signal as a B signal by color separation. Subsequently, as illustrated in FIG. 13, the image pickup signals of the images respectively picked up in the pixel 23G and the pixel 23B are added in the addition processing circuit 37.

For example, signals of images picked up in the pixels 23R, 23G and 23B under the first illuminating light L1_1 and the fourth illuminating light L4_1 in the illumination period T1 are outputted by the color separation circuit 35 as output signals obtained by image pickup signals of R(L1_1), G(L4_1) and B(L4_1) being subjected to color separation, from the output terminals 35a, 35b and 35c.

When illumination is performed with the second illuminating light L2 (600 nm) and the third illuminating light L3 (460 nm), the pixel 23R of the image pickup device 19 receives a reflection light of the second illuminating light L2 (600 nm) with a high sensitivity to the reflection light of the second illuminating light L2 (600 nm), the pixel 23G receives the reflection light of the second illuminating light L2 (600 nm) with a lower sensitivity than the pixel 23R, and the pixel 23B receives a reflection light of the third illuminating light L3 (460 nm) with a high sensitivity to the reflection light of the third illuminating light L3 (460 nm).

More specifically, when an image is picked up by the image pickup device 19 including the color filter 22 in a case where illumination is performed with use of the second filter 62b having (transmittance of) peak at 600 nm and 460 nm, images of the reflection light of the second illuminating light L2 that reaches the peak at 600 nm, and an image of the reflection light of the third illuminating light L3 that reaches the peak at 460 nm can be respectively picked up by being separated without colors being mixed by the pixel 23R of the R filter 22R and the pixel 23B of the B filter 22B.

As described in the first modification, in the case where an image of the reflection light of the second illuminating light L2 that reaches the peak at 600 nm is picked up, the output signals of the color separation circuit 35 are added in the addition processing circuit 37 since the pixels 23R and 23G have sensitivities.

For example, signals of an image picked up by the pixels 23R, 23G and 23B under the second illuminating light L2_2 and the third illuminating light L3_2 in the illumination period T2 in FIG. 13 are outputted by the color separation circuit 35 as output signals obtained by image pickup signals of R (L2_2), G(L2_2) and B(L3_2) being subjected to color separation, from the output terminals 35a, 35b and 35c in the illumination period T3 after the illumination period T2 ends.

In the illumination period T3 and the following periods, the operations in the illumination periods T1 and T2 are repeated.

As shown in FIG. 13, (the second addition processing circuit 37c and the first addition processing circuit 37b of) the addition processing circuit 37 alternately outputs a second addition signal B(L4_1)+G(L4_1) obtained by adding the image pickup signals B(L4_1) and G(L4_1), and a first addition signal G (L2_2)+R(L2_2) obtained by adding the image pickup signals G(L2_2) and R(L2_2). Note that in FIG. 13, image pickup signal outputs (R) and (B') that are not added are shown as addition processing outputs, together with the addition processing outputs 37b(G) and 37c(B). As shown in FIG. 13, the image pickup signals (including the case of the addition signal which is added) that are outputted as the addition processing outputs (R), 37b(G), 37c(B) and (B') from the addition processing circuit 37 are respectively stored in the memories 39R, 39G, 39B and 39B' in the synchronization circuit 38.

Subsequently, in accordance with selection by the user as described above, one image pickup signal in the image pickup signals of B images which are picked up under the fourth illuminating light L4 of 540 nm and the third illuminating light L3 of 460 nm and are stored in the B memories 39B and 39B' can be selected.

When a first image is selected, images that are picked up under the illuminating lights of 630 nm, 600 nm and 460 nm are displayed in the color monitor 5 as the R, G and B images, and when a second image is selected, images that are picked up under the illuminating lights of 630 nm, 600 nm and 540 nm are displayed as the R, G and B images.

According to the present modification, the images picked up under illumination of different narrow band lights can be selected. Further, in the present modification, addition signals are generated in the addition processing circuit 37, and therefore, an image pickup signal (or an image signal) with a favorable SNR can be generated (or acquired). Accordingly, an endoscopic image with good image quality can be displayed, and can be effectively used when diagnosis and treatment are performed.

Note that in the present modification, the case where the first illuminating light L1 of 630 nm and the fourth illuminating light L4 of 540 nm are simultaneously emitted, the second illuminating light L2 of 600 nm and the third illuminating light L3 of 460 nm are simultaneously emitted and the former and the latter are alternately emitted are explained, but the combinations that are simultaneously emitted may be changed.

More specifically, the first illuminating light L1 of 630 nm and the third illuminating light L3 of 460 nm are simultaneously emitted, the second illuminating light L2 of 600 nm and the fourth illuminating light L4 of 540 nm are simultaneously emitted, and the former and the latter may be alternately emitted.

Figure 14:
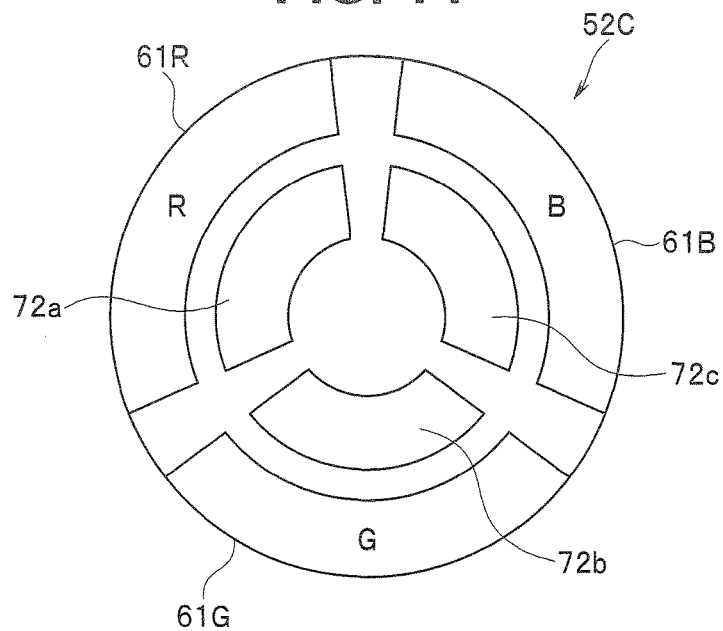
FIG. 14 is a view showing a rotary filter in a third modification.
Figure 15:
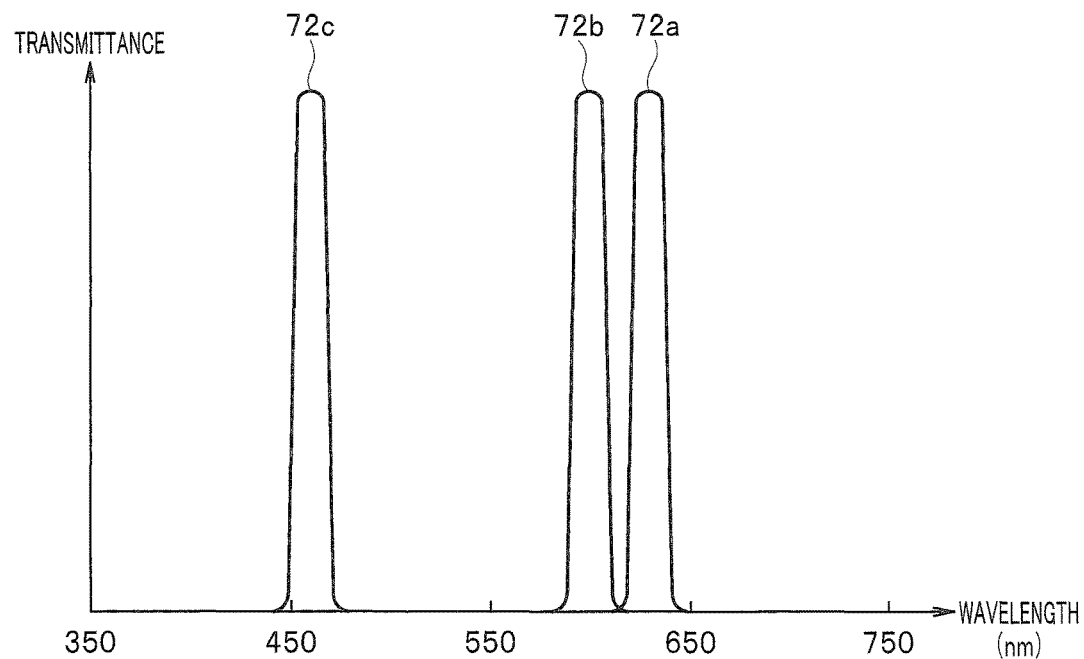
FIG. 15 is a diagram showing spectral characteristics of three filters provided in the rotary filter in FIG. 14.

Note that in the endoscope apparatus of the first modification shown in FIG. 7, a rotary filter 52C shown in FIG. 14 may be adopted instead of the rotary filter 52 shown in FIG. 8. The rotary filter 52C adopts a configuration in which three filters 72a, 72b and 72c that respectively transmit only narrow band lights of 630 nm, 600 nm and 460 nm are provided in a circumferential direction instead of the first filter 62a and the second filter 62b at the inner circumferential side in FIG. 8. FIG. 15 shows transmission characteristics of the three filters 72a, 72b and 72c.

In the case of the present modification, the color filter 22 that optically separate colors is unnecessary, and a color separation circuit that electrically separates colors is also unnecessary.

Note that embodiments that are configured by partially combining the aforementioned embodiment and modifications belong to the present invention.

What is claimed is:

1. An endoscope apparatus, comprising:
an image pickup sensor having a first pixel having a sensitivity in a predetermined wavelength band, and a second pixel having a sensitivity in a wavelength band including a part of the predetermined wavelength band;
a light source configured to generate a light for irradiating a subject, the light being narrow band light, return light of the light applied to the subject having an intensity peak in the predetermined wavelength band to which the second pixel has a sensitivity; and
an addition circuit configured to generate an addition signal obtained by adding a first image pickup signal obtained by receiving a return light from the subject at a time of the subject being irradiated in the first pixel, and a second image pickup signal obtained by receiving a return light from the subject in the second pixel,
wherein the light source further generates a first light, the first light being a light having an intensity which reaches a peak in the part of the predetermined wavelength band to which the second pixel has a sensitivity, and the first light source further generates a second light having an intensity which reaches a peak in the predetermined wavelength band at a timing different from the first light,
the endoscope apparatus further comprising an image generation circuit configured to generate an image in which the addition signal and a third image pickup signal are respectively assigned to different colors, the third image pickup signal being obtained by receiving a return light of the subject at a time of the second light being irradiated in the first pixel.

2. The endoscope apparatus according to claim 1,
wherein the light source further generates a third light that is a light in a wavelength band to which the first pixel and the second pixel do not have sensitivities,
the image pickup sensor further has a third pixel having a sensitivity to the wavelength band of the third light, and
the image generation circuit generates an image in which the addition signal generated in the addition circuit, the first image pickup signal obtained by receiving the return light from the subject at the time of the first light being irradiated in the first pixel, and a fourth image pickup signal obtained by receiving a return light from the subject at a time of the third light being irradiated in the third pixel are respectively assigned to different colors.

3. The endoscope apparatus according to claim 2,
wherein the light source comprises a first light source, a second light source and a third light source configured to generate the first light, the second light and the third light, respectively, and
further has a light emission control circuit configured to perform control of respective light emissions of the first light source, the second light source and the third light source, and
the light emission control circuit performs control of causing the first light source and the second light source to emit lights alternately, and causing the third light source to emit light continuously.

4. The endoscope apparatus according to claim 2,
wherein the light source comprises a first light source configured to generate the first light and the third light simultaneously, and a second light source configured to generate the second light and the third light simultaneously, and
further comprises a light emission control circuit configured to perform control of performing light emissions of the first light source and the second light source alternately.

5. The endoscope apparatus according to claim 2,
wherein the image pickup sensor comprises first and second color filters that have transmittances that respectively transmit the first light and the second light, and a third color filter having a transmittance that transmits only the third light, and
is configured by a color image pickup sensor in which the first pixel, the second pixel and the third pixel are respectively formed of pixels that receive lights that are respectively transmitted through the first, the second and the third color filters.

6. The endoscope apparatus according to claim 2,
wherein the light source comprises a first light source configured to simultaneously generate the first light, and the third light to which only the third pixel has a sensitivity, and a second light source configured to simultaneously generate the second light, and a fourth light to which the second pixel and the third pixel have sensitivities,
the addition circuit generates the first addition signal which is the addition signal obtained by adding the first image pickup signal obtained by receiving the return light from the subject at the time of the subject being irradiated with the light in the first pixel, and the second image pickup signal obtained by receiving the return light from the subject in the second pixel, and generates a third addition signal obtained by adding a sixth and a seventh image pickup signals obtained by respectively receiving a return light from the subject at a time of the fourth light being irradiated, by the second pixel and the third pixel, a light emission control circuit configured to perform control of causing the first light source and the second light source to emit light alternately is further included, and the image generation circuit generates an image in which the first addition signal and the third addition signal are respectively assigned to different colors, and generates one selected from two images generated under the third light and the fourth light as an image assigned to one color.

7. The endoscope apparatus according to claim 1, wherein an intensity of the second light further reaches a peak in a wavelength different from the first light within the part of the predetermined wavelength band to which the second pixel has a sensitivity, the addition circuit further generates a first addition signal which is the addition signal obtained by adding the first image pickup signal obtained by receiving the return light from the subject at the time of the subject being irradiated with the light in the first pixel, and the second image pickup signal obtained by receiving the return light from the subject in the second pixel, and generates a second addition signal obtained by adding a fifth image pickup signal obtained by receiving a return light from the subject at a time of the second light being irradiated in the first pixel, and a sixth image pickup signal obtained by receiving a return light from the subject at a time of the second light being irradiated in the second pixel, and the image generation circuit generates an image in which the first addition signal and the second addition signal which are generated in the addition circuit are respectively assigned to different colors.

8. The endoscope apparatus according to claim 7, wherein the image pickup sensor further has a third pixel having a sensitivity to a wavelength band to which the first pixel and the second pixel do not have sensitivities, the endoscope apparatus further comprising: a light adjusting circuit configured to generate a light adjustment signal for performing light adjustment based on the first addition signal, the second addition signal, and an image pickup signal by the third pixel, wherein by the light adjustment signal, a light emission amount of the first light and a light emission amount of the second light in the light source are adjusted, and brightness of an image displayed in a display is adjusted.

9. The endoscope apparatus according to claim 1, wherein the light source generates narrow band lights of wavelengths of 600 nm and 630 nm, or wavelengths of 630 nm and 600 nm, as the first and the second lights.

* * * * *